(12) United States Patent
Li et al.

(10) Patent No.: US 7,087,086 B2
(45) Date of Patent: Aug. 8, 2006

(54) BIOLOGICAL AGENT-CONTAINING CERAMIC COATING AND METHOD

(75) Inventors: Panjian Li, Fort Wayne, IN (US); Hai Bo Wen, Warsaw, IN (US); Elizabeth A. Hippensteel, North Manchester, IN (US)

(73) Assignee: Depuy Products, Inc., Warsaw, IN (US)

( * ) Notice: Subject to any disclaimer, the term of this patent is extended or adjusted under 35 U.S.C. 154(b) by 552 days.

(21) Appl. No.: 10/355,827

(22) Filed: Jan. 31, 2003

(65) Prior Publication Data

US 2004/0153165 A1     Aug. 5, 2004

(51) Int. Cl.
*A61F 2/28* (2006.01)
(52) U.S. Cl. .................................. 623/23.57
(58) Field of Classification Search ............ 623/23.57, 623/23.56, 23.58, 11.11, 16.11, 17.11, 18.11; 427/2.24; 424/422
See application file for complete search history.

(56) References Cited

U.S. PATENT DOCUMENTS

| | | | |
|---|---|---|---|
| 4,596,574 A | 6/1986 | Urist | |
| 5,068,122 A * | 11/1991 | Kokubo et al. | 427/2.1 |
| 5,258,029 A | 11/1993 | Chu et al. | |
| 5,441,536 A * | 8/1995 | Aoki et al. | 427/2.27 |
| 5,947,893 A | 9/1999 | Agrawal et al. | |
| 6,129,928 A | 10/2000 | Sarangapani et al. | |
| 6,139,585 A | 10/2000 | Li | |
| 6,143,948 A | 11/2000 | Leitao et al. | |
| 6,180,606 B1 | 1/2001 | Chen et al. | |
| 6,280,789 B1 | 8/2001 | Rey et al. | |
| 6,312,468 B1 * | 11/2001 | Best et al. | 623/16.11 |
| 6,461,385 B1 | 10/2002 | Gayer et al. | |
| 2001/0038848 A1 | 11/2001 | Donda et al. | |
| 2001/0053406 A1 * | 12/2001 | Layrolle et al. | 427/2.27 |

FOREIGN PATENT DOCUMENTS

| | | | |
|---|---|---|---|
| WO | WO 97141273 | * | 11/1997 |
| WO | WO 01/83367 A2 | | 11/2001 |

OTHER PUBLICATIONS

Agrawal et al., "Protein release kinetics of a biodegradable implant for fracture non-unions," *Biomaterials*, 16 (16), 1255-1260 (1995).
De Bruijn et al., "New developments in implant coatings: biomimetics and tissue engineering," Biomaterials in Surgery, Walenkamp, Stuttgart: Geory Thieme Verlag, 77-82 (1998).
Ducheyne et al., "The effect of calcium phosphase ceramic composition and structure on *in vitro* behavior. I. dissolution," *Journal of Biomedical Materials Research*, 27, 25-34 (1993).
Liu et al., "Biomimetic coprecipitation of calcium phosphate and bovine serum albumin on titanium alloy," *Journal of Biomedical Materials Research*, 56 (1), 327-335 (2001).
Liu et al., "Proteins incorporated into biomimetically prepared calcium phosphate coatings modulate their mechanical strength and dissolution rate," *Biomaterials*, 24, 65-70 (2003).
Meraw et al., "Use of alendronate in peri-implant defect regeneration," *Journal of Periodontol*, 70 (2), 151-158 (1999).
Radin et al., "Calcium phosphate ceramic coatings as carriers of vancomycin," *Biomaterials*, 18 (11), 777-782 (1997).
Wen et al., "Incorporation of bovine serum albumin in calcium phosphate coating on titanium," *Journal of Biomedical Materials Research*, 46 (2), 245-252 (1999).

* cited by examiner

*Primary Examiner*—Eduardo C. Robert
*Assistant Examiner*—David Comstock
(74) *Attorney, Agent, or Firm*—Leydig Voit & Mayer, Ltd.

(57) ABSTRACT

The invention provides an implantable article, a method of preparing the same, and methods of modifying a ceramic-coated implantable article. The implantable article comprises a biocompatible substrate and a bioactive ceramic surface coating into which a biological agent is incorporated. The preparation and modification of an implantable article involve incubating a biocompatible substrate surface or pre-existing ceramic coating thereon with a composition comprising (i) a biological agent, (ii) calcium ions, (iii) phosphate ions, and (iv) a liquid carrier.

36 Claims, No Drawings

BIOLOGICAL AGENT-CONTAINING CERAMIC COATING AND METHOD

FIELD OF THE INVENTION

The invention pertains to an implantable article, a method of preparing the same, and methods of modifying a ceramic-coated implantable article.

BACKGROUND OF THE INVENTION

It is desirable to apply mineralized and/or ceramic coatings to a variety of articles. Biological implants (e.g., medical implants) represent one class of articles to which such coatings are frequently applied. The substrate to which such a coating is applied is usually a metal or a plastic, but the coating can be applied to other substrates such as ceramic and silicon.

Biological implants, such as joint and dental prostheses, usually must be permanently affixed or anchored within bone. In some instances it is acceptable to use a bone cement to affix the prosthesis within bone. In the case of many joint prostheses, however, it is now more common to affix the joint prosthesis by encouraging natural bone ingrowth in and around the prosthesis. Bone-to-implant interfaces that result from natural bone ingrowth tend to be stronger over time and more permanent than are bone cement-prosthesis bonds.

Optimal bone ingrowth requires that natural bone grow into and around the prosthesis to be implanted. Bone ingrowth and prosthesis fixation can be enhanced by providing irregular beaded or porous surfaces on the implant. Although various materials, including titanium alloys, are biocompatible, they are not necessarily bioactive because they can neither conduct bone formation nor form chemical bonds with bone.

Thus, enhanced fixation of implants within bone can be attained by coating the implant with a bioactive mineralized and/or ceramic material. Such coatings have been shown to encourage more rapid bone ingrowth in and around the prosthesis.

Various techniques are used to apply mineralized and/or ceramic coatings to bioimplantable substrates. These coatings are typically made of ceramics and tend to be characterized by a relatively large crystal size. These coatings can be applied by a variety of techniques including plasma spraying, ion implantation, and sol-gel processing. These coating methods, although relatively widely used, do have some drawbacks. For example, the applied coatings tend to possess micropores and macropores, and they can be relatively thick and brittle. These coatings can also possess chemical defects, and they do not always adhere well to substrates. Finally, such coatings are not evenly and uniformly applied to surfaces with complex geometries, such as porous surfaces with undercut regions. Moreover, surfaces having such complex geometries are not completely coated.

It has been well documented that calcium phosphate ceramics, especially hydroxyapatite, can conduct bone formation. Hydroxyapatite ceramic has been successfully applied as a coating on cementless metallic implants to achieve quick and strong fixation. Thermal plasma spraying is one of the more common methods used to produce hydroxyapatite coatings. However, the resulting plasma-sprayed hydroxyapatite coating is of relatively low density and is not uniform in structure or composition. The adhesion between the coating and substrate is generally not very strong, especially after long-term exposure within the body. The generation of hard ceramic particles, resulting from the degradation of thermal plasma sprayed coating, and coating delamination, are major concerns.

Low temperature processes have also been implemented to produce apatite ceramic coatings using water-based solutions. Since aqueous solutions can reach any open space, these low-temperature processes can be efficiently used in the case of substrates with complex surface geometries. The hydroxyapatite coating that is formed from this solution can be more biologically friendly to bone tissue than is the plasma-sprayed hydroxyapatite coating which is produced by a high temperature process. However, currently known low temperature processes typically require pretreatment of the substrate.

One example of an aqueous system-based coating technique is disclosed in U.S. Pat. No. 5,205,921 in which bioactive ceramic coatings are electrodeposited upon a substrate. Bunker et al., *Science* 264: 48–55 (1994) disclose a technique for applying an octacalcium phosphate upon a substrate by immersing the substrate in a solution containing calcium chloride after surface treating the substrate with a material such as chlorosilane. Other techniques, such as disclosed in Japanese Patent Application No. 8-40711, form a hydroxyapatite coating by exposing the substrate to calcium phosphate in a pressure reactor. U.S. Pat. No. 5,188,670 discloses a technique for forming a hydroxyapatite coating on a substrate by directing a stream of liquid containing hydroxyapatite particles to apply a fibrous, crystalline coating of hydroxyapatite.

Bioactive ceramic coatings, such as those described above, have been improved upon with respect to the ability to induce or conduct bone formation, namely, by incorporating into the pores of the ceramic coating a biological agent. For instance, U.S. Pat. No. 5,947,893 discloses a medical device having a tissue-mating surface, the pores of which are impregnated with a composition of a pharmaceutically active substance and a biodegradable carrier. Also, U.S. Pat. No. 4,596,574 describes a biodegradable porous ceramic delivery system useful for the delivery of the bone morphogenic protein (BMP). U.S. Pat. No. 6,180,606 B1 discloses osteogenic compositions comprising a porous or semi-porous matrix, an osteogenic factor, and an agent, such as a growth factor, nutrient factor, drug, calcium-containing compound, blood product, and protein. See also U.S Pat. No. 5,258,029. A biomimetic calcium phosphate coating having a growth factor covalently bound thereto that is coated with a hydrogel is described in U.S. Pat. No. 6,129,928. Biomimetic co-precipitation of bovine serum albumin (BSA), $Ca^{2+}$, and $PO_4^{3-}$ onto a titanium substrate is described in Liu et al., *Biomaterials* 24: 65–70 (2003). See also U.S. Pat. No. 6,143,948; Liu et al., *J. Biomed. Mat. Res.* 57: 327–335 (2001); and Wen et al., *J. Biomed. Mat. Res.* 46: 245–252 (1999). The incorporation of the antibiotic, vancomycin, into a ceramic coating is disclosed by Radin et al., *Biomaterials* 18: 777–782 (1997).

Despite the existence of numerous ceramic coatings and the various processes for producing such coatings, there remains a need for implantable articles having improved and reliable bioactive ceramic coatings into which biological agents are incorporated and methods of making the same.

The invention provides such implantable articles, which have improved ceramic coatings. The invention further provides methods of making the same. These and other advantages of the invention, as well as additional inventive features, will be apparent from the description of the invention provided herein.

BRIEF SUMMARY OF THE INVENTION

The invention provides an implantable article comprising (i) a biocompatible substrate and (ii) a bioactive surface coating chemically bonded to a substrate surface over at least a portion of the substrate, wherein the coating comprises a non-hydroxyl containing carbonated calcium phosphate bone mineral nanocrystalline apatite with chemically adsorbed water, wherein the coating has a crystal size less than about 1 µm and has pores that are less than 1 µm in diameter, and wherein a biological agent is incorporated into the pores.

The invention also provides a method of preparing an implantable article. The method comprises (a) providing a biocompatible substrate, (b) incubating at least a portion of a surface of the biocompatible substrate with a composition comprising (i) a biological agent, (ii) calcium ions in a concentration of about 1 mM to about 10 mM, (iii) phosphate ions in a concentration of about 1 mM to about 10 mM, and (iv) a liquid carrier, wherein the pH of the composition is between about 3.5 to about 9, and (c) removing the liquid carrier from the biocompatible substrate to yield an implantable article with a bioactive surface coating chemically bonded to a substrate surface over at least a portion of the substrate, wherein the coating comprises a non-hydroxyl containing carbonated calcium phosphate bone mineral nanocrystalline apatite with chemically adsorbed water, wherein the coating has a crystal size less than about 1 µm and has pores that are less than 1 µm in diameter, and wherein a biological agent is incorporated into the pores.

The invention further provides methods of modifying a ceramic-coated implantable article. One method comprises (a) providing an implantable article comprising a biocompatible substrate with a bioactive ceramic coating on at least a portion of the surface of the biocompatible substrate, (b) incubating at least a portion of the bioactive ceramic coating with a composition comprising (i) a biological agent, (ii) calcium ions in a concentration of about 0.01 mM to about 1 mM, (iii) phosphate ions in a concentration of about 0.01 mM to about 1 mM, and (iv) a liquid carrier, wherein the pH of the composition is between about 3.5 to about 9, and (c) removing the liquid carrier from the bioactive ceramic coating to yield a modified implantable article with a bioactive ceramic coating into which the biological agent is incorporated. Another method comprises (a) providing an implantable article comprising a biocompatible substrate with a bioactive ceramic coating on at least a portion of the surface of the biocompatible substrate, wherein the bioactive ceramic coating comprises carbonated apatite of a first morphology, (b) incubating at least a portion of the bioactive ceramic coating with a composition comprising (i) a biological agent, (ii) calcium ions in a concentration of about 1 mM to about 10 mM, (iii) phosphate ions in a concentration of about 1 mM to about 10 mM, and (iv) a liquid carrier, wherein the pH of the composition is between about 3.5 to about 9, and (c) removing the liquid carrier from the bioactive ceramic coating to yield a modified implantable article with a bioactive ceramic coating into which the biological agent is incorporated, wherein the bioactive ceramic coating of the modified implantable article (i) has a second morphology that differs from the first morphology and (ii) does not comprise carbonated hydroxyapatite. The modified implantable articles yielded by either of these inventive methods are also provided.

DETAILED DESCRIPTION OF THE INVENTION

The invention provides an implantable article, a method of preparing an implantable article, and methods of modifying a ceramic-coated implantable article. The implantable article comprises a biocompatible substrate and a bioactive surface or ceramic coating that is either created or modified on a least a portion of the surface of the biocompatible substrate such that the bioactive surface or ceramic coating incorporates a biological agent.

The invention provides an implantable article comprising (i) a biocompatible substrate and (ii) a bioactive surface coating chemically bonded to a substrate surface over at least a portion of the substrate. The coating comprises a non-hydroxyl containing carbonated calcium phosphate bone mineral nanocrystalline apatite with chemically adsorbed water. The coating has a crystal size of less than about 1 µm and has pores that are less than 1 µm in diameter. A biological agent is incorporated into the pores of the coating.

The invention also provides a method of preparing an implantable article. The method comprises, consists essentially of, or consists of (a) providing a biocompatible substrate, (b) incubating at least a portion of a surface of the biocompatible substrate with a composition comprising (i) a biological agent, (ii) calcium ions in a concentration of about 1 mM to about 10 mM, (iii) phosphate ions in a concentration of about 1 mM to about 10 mM, and (iv) a liquid carrier, wherein the pH of the composition is between about 3.5 to about 9, and (c) removing the liquid carrier from the biocompatible substrate to yield an implantable article with a bioactive ceramic coating chemically bonded to a substrate surface over at least a portion of the substrate, wherein the coating comprises a non-hydroxyl containing carbonated calcium phosphate bone mineral nanocrystalline apatite with chemically adsorbed water, wherein the coating has a crystal size less than about 1 µm and has pores that are less than 1 µm in diameter, and wherein a biological agent is incorporated into the pores of the coating.

The invention further provides methods of modifying an implantable article, as well as the modified implantable articles yielded (or provided) by such methods. These methods are particularly suited to the modification of a ceramic-coated implantable article.

The first method comprises (a) providing an implantable article comprising a biocompatible substrate with a bioactive ceramic coating on at least a portion of the surface of the biocompatible substrate, (b) incubating at least a portion of the bioactive ceramic coating with a composition comprising (i) a biological agent, (ii) calcium ions in a concentration of about 0.01 mM to about 1 mM, (iii) phosphate ions in a concentration of about 0.01 mM to about 1 mM, and (iv) a liquid carrier, wherein the pH of the composition is between about 3.5 to about 9, and (c) removing the liquid carrier from the bioactive ceramic coating to yield a modified implantable article with a bioactive ceramic coating into which the biological agent is incorporated.

The second method comprises (a) providing an implantable article comprising a biocompatible substrate with a bioactive ceramic coating on at least a portion of the surface of the biocompatible substrate, wherein the bioactive ceramic coating comprises carbonated apatite of a first morphology, (b) incubating at least a portion of the bioactive ceramic coating with a composition comprising (i) a biological agent, (ii) calcium ions in a concentration of about 1 mM to about 10 mM, (iii) phosphate ions in a concentration of about 1 mM to about 10 mM, and (iv) a liquid carrier, wherein the pH of the composition is between about 3.5 to about 9, and (c) removing the liquid carrier from the bioactive ceramic coating to yield a modified implantable article with a bioactive ceramic coating into which the biological agent is incorporated, wherein the bioactive ceramic coating of the modified implantable article (i) has a second morphology that differs from the first morphology and (ii) does not comprise carbonated hydroxyapatite.

The term "implantable article" as used herein refers to any object or device that can be inserted or embedded into or grafted onto a body, or any part thereof, and that is designed for biomedical use. The implantable article, for example, can be a bone substitute, a joint prosthesis, a dental implant (prosthodontics), a maxillofacial implant, a vertebral surgery aid, a transcutaneous device (stoma or the like), or other medical or cosmetic device. Such implantable articles can serve as a bone replacement or bone reinforcement, as well as a means of fixing a device to a particular bone.

By "biocompatible substrate" is meant any object or device that is compatible with the body into which the object or device is inserted or embedded or with the body onto which the object or device is grafted, such that the object or device will not cause an adverse immune response in the body. The biocompatible substrate can comprise any suitable material(s), such as silicon, metals, ceramics, or polymers. Biocompatible metals include titanium, tantalum, niobium, zirconium, and alloys thereof (e.g., titanium alloys and tantalum alloys), as well as cobalt-chromium alloys and stainless steel. Biocompatible polymers can be natural or synthetic polymers, such as polyethylene (e.g., ultrahigh molecular weight polyethylene or polyethylene oxide), polypropylene, polytetrafluoroethylene, polyglycolic acid, polylactic acid, other polysaccharides, and copolymers of any of the foregoing (e.g., copolymers of polylactic acid and polyglycol acid). Preferably, the biocompatible substrate comprises, consists essentially of, or consists of a biocompatible metal. More preferably, the biocompatible substrate comprises, consists essentially of, or consists of titanium. The biocompatible substrate can be any suitable portion of the implantable article, preferably a component of a prosthesis (particularly a joint prosthesis).

The biocompatible substrate can be modified in a variety of ways prior to being coated with the bioactive surface or ceramic coating. For example, the biocompatible substrate can be modified with respect to surface roughness in order to facilitate the adherence of the bioactive surface or ceramic coating to the biocompatible substrate. Methods of modifying the surface roughness of a biocompatible substrate are known in the art and include, for instance, acid etching and grit blasting. The biocompatible substrate typically is subjected to a cleaning process (e.g., after modifying the surface roughness), such as ultrasonic cleaning. Such cleaning processes are also known in the art. Preferably, the biocompatible substrate is grit-blasted and then ultrasonically cleaned.

The bioactive surface or ceramic coating coats a least a portion of the biocompatible substrate and can coat the entire surface of the biocompatible substrate. By "bioactive" is meant having the ability to effect local tissue activity, for instance, by improving local bone formation or by preventing the onset and proliferation of microbial species. The bioactive surface coating typically will be a ceramic coating, i.e., a coating that is predominantly of ceramic material(s). The bioactive ceramic coating can comprise, consist essentially of, or consist of any suitable ceramic material(s). Suitable ceramic materials include calcium phosphate, alumina, bioglass, and composite materials containing one or more of a biodegradable alkali metal salt, alkaline earth metal salt, or transition metal salt. Preferred ceramic materials are those containing calcium and phosphate, such as apatite, carbonated apatite, carbonated hydroxyapatite, tricalcium phosphate, octacalcium phosphate, and beta tricalcium phosphate.

The bioactive surface or ceramic coating can comprise multiple (i.e., two or more) layers, which may be the same or different. The bioactive surface or ceramic coating can be of any suitable thickness. The bioactive surface or ceramic coating desirably has a thickness of about 0.005 μm or more (e.g., about 0.01 μm or more, about 0.1 μm or more, or about 0.2 μm or more). The bioactive surface or ceramic coating desirably has a thickness of about 50 μm or less (e.g., about 30 μm or less, about 20 μm or less, about 10 μm or less, or about 5 μm or less).

The bioactive surface or ceramic coating can contain any suitable components, substances, and chemical groups and ions. The bioactive surface or ceramic coating preferably contains one or more substances selected from the group consisting of sodium, calcium, magnesium, sulfate, silicate, chloride, and mixtures thereof. The bioactive surface or ceramic coating can contain any suitable ratios of components, substances, and chemical groups and ions. The bioactive surface or ceramic coating preferably contains carbonate groups and phosphate groups. In such an event, the bioactive surface or ceramic coating desirably contains a molar ratio of carbonate groups to phosphate groups of about 1:100 to 1:3. The bioactive surface or ceramic coating also preferably contains magnesium. When the coating contains both magnesium and calcium, the atomic ratio of magnesium to calcium present in the bioactive surface or ceramic coating is about 1:5000 to about 1:4 (e.g., about 1:2500 to about 1:4, about 1:1000 to about 1:5, about 1:500 to about 1:5, about 1:100 to about 1:4, about 1:50 to about 1:10, or about 1:30 to about 10).

Suitable biocompatible substrates and suitable bioactive surface and ceramic coatings, as well as implantable articles, are described in U.S. Pat. Nos. 6,139,585 and 6,143,948.

Preferably, the bioactive surface or ceramic coating is a nanoporous ceramic coating. The term "nanoporous" as used herein refers to the coating having pores that are less than 1 μm in diameter. Also preferred is that the bioactive surface or ceramic coating is nanocrystalline. The term "nanocrystalline" as used herein means having a crystal size of less than 1 μm. Nanoporous, nanocrystalline ceramic-coated implantable articles are commercially available from DePuy Orthopaedics, Inc. (Warsaw, Ind.).

The bioactive surface or ceramic coating preferably is chemically bonded the surface of the biocompatible substrate. The bioactive surface or ceramic coating preferably comprises a non-hydroxyl containing carbonated calcium phosphate bone mineral nanocrystalline apatite with chemically adsorbed water, wherein the coating has a crystal size less than 1 μm and has pores that are less than 1 μm in diameter. The term "non-hydroxyl containing" as used herein refers to an absence of hydroxyl (OH) groups. The term "carbonated calcium phosphate bone mineral" refers to a substance that is similar to or the same as bone that has carbonate, calcium, and phosphate ions. The term "apatite" as used herein refers to any of a group of calcium phosphate minerals occurring variously as hexagonal crystals, as granular masses, or in fine-grained masses.

The term "biological agent" refers to any naturally-occurring or synthetic agent that has a biological effect. Suitable biological agents include proteins, lipids, (lipo) polysaccharides, growth factors, cytostatic agents, hormones, antibiotics, anti-infective agents, anti-allergenic agents, anti-inflammatory agents, progestational agents, humoral agents, antipyretic agents, and nutritional agents. Preferably, the biological agent is an osteoinductive substance, osteoconductive substance, or a substance that is both osteoinductive and osteoconductive. The term "osteoinductive" as used herein refers to an agent that promotes mitogenesis of undifferentiated perivascular mesenchymal cells leading to the formation of osteoprogenitor cells with the capacity to form new bone. The term "osteoconductive" as used herein means promoting the facilitation of blood vessel incursion and new bone formation into a defined passive trellis structure. In other words, "osteoconductive" generally refers to factors that create a favorable environment for new bone growth and apposition, while "osteoinductive" generally refers to factors that stimulate, either directly or indirectly, the new bone growth. The term "apposition" as used herein refers to bone formation directly on the bioactive surface. The biological agent that is osteoinductive, osteoconductive, or both is preferably a protein. Osteoinductive proteins are known in the art and include, for example, Bone Morphogenic Protein (BMP) and Osteogenic Protein-1 (OP-1; BMP-7). Osteoconductive proteins are also known in the art and include, for example, extracellular matrix proteins, such as collagen, antimicrobial and anti-inflammatory proteins, and blood-clotting factors. Proteins that are both osteoinductive and osteoconductive include, for instance, BMP and OP-1. Preferably, the protein is a non-collagenous bone protein, wherein the term "non-collagenous" means that it is not collagen. Non-collagenous bone proteins include, for example, osteonectin, osteopontin, osteocalcin, and bone sialoprotein. Also preferred is that the protein is a growth factor, such as Fibroblast Growth Factor (FGF), Transforming Growth Factor-β (TGF-β), Platelet-Derived Growth Factor (PDGF), Insulin Growth Factor (IGF), and family members of any of the foregoing. Suitable biological agents also include antibiotics, such as vancomycin, penicillin, tetracycline, chlortetracycline, bacitracin, nystatin, streptomycin, neomycin, polymyxin, gramicidin, oxytetracycline, chloramphenicol, and erythromycin.

The composition used to form the bioactive surface or ceramic coating incorporating a biological agent (either by creating such a coating or modifying an existing coating) on a biocompatible substrate comprises (i) a biological agent, (ii) calcium ions, (iii) phosphate ions, and (iv) a liquid carrier. The terms "calcium ions" and "phosphate ions" refer to ions that include calcium and ions that include the phosphate group, respectively. The ions can be, for example, monovalent, divalent, or trivalent with respect to charge. The calcium ions preferably are divalent, i.e., $Ca^{2+}$. The phosphate ions preferably are $PO_4^{3-}$, $HPO_4^{2-}$, or $H_2PO_4^-$. The concentrations of the calcium ions and the phosphate ions are independent, i.e., the concentrations can be the same or different. The concentration of each of the calcium ions and the phosphate ions in the composition of the first method of modifying a ceramic-coated implantable article described herein is about 0.01 mM to about 1 mM. Preferably, the concentration of each is about 0.5 mM or less. More preferred is that the concentration of each is about 0.2 mM or less. Also preferred is that the concentration of each of the calcium ions and phosphate ions is about 0.05 mM or more. The concentration of each of the calcium ions and the phosphate ions in the composition of the second method of modifying a ceramic-coated implantable article described herein is about 1 mM to about 10 mM. Preferably, the concentration of each is about 1 mM to about 5 mM. The concentration of the calcium ions is more preferably about 2 mM to about 3 mM, whereas the concentration of the phosphate ions is more preferably about 3 mM to about 4 mM.

The composition can further comprise additional components, substances, and chemical groups and ions. For example, the composition can further comprises one or more substances selected from the group consisting of sodium, potassium, magnesium, silicate, chloride, $SO_4^{2-}$, tris(hydroxymethyl)aminomethane, and mixtures thereof.

The liquid carrier can be any suitable aqueous or non-aqueous liquid in which at least calcium ions, phosphate ions, and the biological agent can be suspended or dissolved for delivery of these components to the biocompatible substrate and/or bioactive surface or ceramic coating. Suitable liquid carriers include water, tris-buffered saline, phosphate-buffered saline, and the like. The liquid carrier preferably is a physiologically compatible carrier, more preferably water (e.g., purified or sterilized water).

The pH of the composition used to form the bioactive surface or ceramic coating is between about 3.5 to about 9. Preferably, the pH is between about 5 and about 8.5. More preferably, the pH is between about 6.5 and about 8.

The incubation time with the composition in accordance with the inventive methods typically is about 30 minutes or more. Suitable incubation times include about 1 hour or more, about 5 hours or more, about 10 hours or more, about 24 hours or more, about 48 hours or more, about 72 hours or more, and about 100 hours or more. The incubation time coating preferably is about 12 hours or more. More preferably, the incubation time is about 24 hours or more. The incubation time most preferably is about 72 hours or more. In general, longer incubation times provide greater concentrations of the biological agent incorporated into the bioactive surface or ceramic coating.

The temperature at which the incubation with the composition takes place can be any suitable temperature. The incubation temperature typically is about 20° C. to about the temperature at which the biological agent is inactivated or denatured. The temperature at which the biological agent is inactivated or denatured depends upon the specific biological agent. When the biological agent is a protein, inactivation or denaturation generally occurs at a temperature of about 65° C. Accordingly, the incubation temperature preferably is between about 30° C. and about 50° C. More preferably, the incubation temperature is about 37° C.

In the inventive methods, the liquid carrier can be removed from the biocompatible substrate and/or bioactive surface or ceramic coating by any suitable method. Typically, the liquid carrier is removed by drying at a temperature below the temperature at which the biological agent is inactivated or denatured. As mentioned above, this temperature depends upon the nature of the biological agent. The drying method can be freeze-drying (so long as the temperature and act of freeze-drying does not adversely affect the biological agent or the biocompatible substrate and/or bioactive surface or ceramic coating). Alternatively, the drying can occur at a higher temperature, e.g., a temperature of about 20° C. or more, yet below the temperature at which the biological agent is inactiviated or denatured. The drying temperature desirably is about 20° C. to about 50° C. (e.g., about 30° C. and about 50° C.).

The liquid carrier also can be removed by rinsing the biocompatible substrate and/or bioactive surface or ceramic coating with an appropriate liquid, especially an aqueous solution, and then drying the ceramic coating as described above. A preferred rinsing liquid is water (e.g., purified or sterilized water).

One of ordinary skill in the art recognizes that it may not be necessary to remove all of the liquid carrier from the biocompatible substrate and/or bioactive surface or ceramic coating. Preferably, however, all or at least substantially all of the liquid carrier is removed from the biocompatible substrate and/or bioactive surface or ceramic coating.

The biological agent is incorporated into the bioactive surface or ceramic coating. By "incorporated" it is meant that the biological agent is chemically and/or electrostatically bonded to, mechanically fixed to, and/or impregnated or entrapped within the bioactive surface or ceramic coating. The biological agent also can be bound or attached to the bioactive surface or the surface of the ceramic coating.

The biological agent can be present in any suitable concentration in the bioactive surface or ceramic coating. Preferably, the concentration of the biological agent incorporated into the bioactive surface or ceramic coating is about 0.001 ng or more biological agent per mg coating when the biological agent is a growth factor. More preferably, the concentration of the biological agent incorporated into the bioactive surface or ceramic coating is about 0.01 ng or more per mg coating. Most preferably, the concentration of the biological agent incorporated into the bioactive surface or ceramic coating is about 0.1 ng or more biological agent per mg coating (e.g., 1 ng or more biological agent per mg coating, or 10 ng or more biological agent per mg coating). Preferably, the concentration of the biological agent incorporated into the bioactive surface or ceramic coating is about 1 µg per mg coating when the biological agent is an antibiotic or a protein that is not a growth factor. More preferably, the concentration of the biological agent incorporated into the bioactive surface or ceramic coating is about 10 µg per mg coating when the biological agent is an antibiotic or a protein that is not a growth factor. Most preferably, the concentration of the biological agent incorporated into the bioactive surface or ceramic coating is about 100 µg per mg coating when the biological agent is an antibiotic or a protein that is not a growth factor.

The total amount of the biological agent incorporated into the bioactive surface or ceramic coating can be any suitable amount. Preferably, the total amount of the biological agent incorporated into the bioactive surface or ceramic coating is at least 1 ng when the biological agent is a growth factor. More preferably, the total amount of the biological agent incorporated into the bioactive surface or ceramic coating is at least 10 ng when the biological agent is a growth factor. Most preferably, the total amount of the biological agent incorporated into the bioactive surface or ceramic coating is at least 100 ng when the biological agent is a growth factor. Preferably, the total amount of the biological agent incorporated into the bioactive surface or ceramic coating is at least 1 µg when the biological agent is an antibiotic or a protein that is not a growth factor. More preferably, the total amount of the biological agent incorporated into the bioactive surface or ceramic coating is at least 10 µg when the biological agent is an antibiotic or a protein that is not a growth factor. Most preferably, the total amount of the biological agent incorporated into the bioactive surface or ceramic coating is at least 100 µg when the biological agent is an antibiotic or a protein that is not a growth factor.

Methods of determining the concentration of a biological agent incorporated into the bioactive surface or ceramic coating are known in the art. Suitable methods include the bicinchnoinic protein assay (BCA) as described further in the examples set forth herein. A BCA kit that is suitable for use in determining the concentration of a biological agent is commercially available through Pierce Inc. (Rockford, Ill.).

The inventive method of preparing an implantable article yields an implantable article with a bioactive ceramic coating chemically bonded to a substrate surface over at least a portion of the substrate, wherein the coating comprises a non-hydroxyl containing carbonated calcium phosphate bone mineral nanocrystalline apatite with chemically adsorbed water, wherein the coating has a crystal size less than about 1 µm and has pores that are less than 1 µm in diameter, and wherein a biological agent is incorporated into the pores of the coating.

In the first inventive method of modifying a ceramic-coated implantable article, the modified implantable article thus yielded comprises carbonated hydroxyapatite when the ceramic coating on the biocompatible substrate of the implantable article initially provided (i.e., provided in step (a) as described above) is a nanoporous, nanocrystalline ceramic coating comprising carbonated apatite. In the second inventive method of modifying a ceramic-coated implantable article, the modified implantable article thus yielded is characterized by having a second morphology that is different from the first morphology of the ceramic coating of the implantable article initially provided (i.e., provided in step (a) as described above). In other words, the second method of modifying a ceramic-coated implantable article described herein yields a modified implantable article having a morphology that is different from the morphology of the carbonated apatite coating on the biocompatible substrate initially provided (i.e., provided in step (a) as described above). Methods of analyzing the morphology and the structure of ceramic coatings are known in the art. Suitable methods include Fourier Transform Infrared (FT-IR) spectroscopy, X-ray diffraction (XRD) crystallography, Scanning Electron Microscopy (SEM), and Reverse-Phase High Performance Liquid Chromatography (RP-HPLC). In addition to having a different morphology, the modified implantable article yielded by the second method of modifying a ceramic-coated implantable article described herein is further characterized by the lack of hydroxyl groups. In this regard, the ceramic coating does not comprise hydroxyapatite.

The inventive methods of preparing and modifying an implantable article can include other steps. For instance, the inventive methods can further comprise, after the incubation step (i.e., after step (b) as described above), a further incubation step with a second composition comprising a liquid carrier and one or more of (i) calcium ions, (ii) phosphate ions, and (iii) a biological agent (e.g., a second composition that does not include a biological agent or includes a different biological agent than used in the first composition). In essence, the biocompatible substrate and/or bioactive surface or ceramic coating can be incubated with a variety of compositions. Such additional compositions can be the same or different, for example, with respect to the presence, absence, or concentration of the biological agent, the presence, absence, or concentration of another biological agent, and/or the concentration or types of the phosphate ions or calcium ions. In this regard, the inventive methods can further comprise incubating steps that differ from the incubation steps described above (i.e., step (b) as described above) with respect to the specific biological agent used in the composition, the number of elements (or components) that comprise the composition, the concentration of each of the elements (or components) of the composition, the pH of the composition, the time of incubation, and/or the temperature at which the incubation occurs.

The implantable article can be implanted in any suitable mammal, and the invention contemplates such a method of using the implantable articles described herein. Suitable mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLE 1

This example demonstrates a method of modifying a ceramic-coated implantable article.

A nano porous nanocrystalline carbonated apatite film was formed on titanium disks 25.2 mm in diameter and 3 mm thick. Alpha Calf Fraction (HyClone Inc., Logan, Utah; calcium concentration <0.25 mM; phosphate concentration <0.16 mM) mixed with 0.02% sodium azide was adjusted to pH 6.9 using 1 N HCl. This solution was aliquoted (100 ml per aliquot) into 118.3 ml glass bottles. Carbonated apatite-coated and non-coated (control) disks were added (one disk per bottle), capped tightly, and allowed to incubate in a humidified incubator at 37° C. Disks were removed from the incubator after 15, 23, or 94 hours, rinsed thoroughly with $H_2O$, and allowed to dry at room temperature.

Upon incubation with the Alpha Calf Fraction solution, the carbonated apatite was transformed into carbonated hydroxyapatite. This is evident from the OH peak at 3568 $cm^{-1}$ on the Fourier Transform-Infrared (FT-IR) spectra. X-ray diffraction (XRD) and scanning electron microscopy (SEM) analyses demonstrated that the carbonated hydroxyapatite had a larger crystal size and exhibited a morphology that is different from that of the carbonated apatite. The peaks found within the range of 2874 $cm^{-1}$ to 2962 $cm^{-1}$, as well as the peaks found within the range of 1538 $cm^{-1}$ to 3307 $cm^{-1}$ suggest that protein was incorporated into the apatite layer. This is further supported by the Energy Dispersive X-ray Spectroscopy (EDS) analysis, which indicated the presence of sulfur and a much higher concentration of carbon in the coating after incubation in the Alpha Calf Fraction solution. These results demonstrate the conversion of a nanoporous apatite coating into a coating consisting of carbonated hydroxyapatite into which proteins are incorporated.

The total amount of protein incorporated into the hydroxyapatite coating was determined through a bicinchnoinic acid (BCA) protein assay (Pierce Inc., Rockford, Ill.). First, the protein in the coating after incubation was collected by dissolving the coating with 50 mM ethylene diaminetriacetic acid (EDTA). Non-coated disks were soaked in 10% sodium dodecyl sulfate (SDS) and boiled in water to collect any adsorbed proteins. The amount of total protein for each sample was determined with a calibration curve based on bovine serum albumin (BSA) standards using an ELX8081U ultra microplate reader (Bio-Tek Instruments Inc., Winooski, Vt.). The results from the BCA assay show an increase in total protein in the coating as the incubation time increased. Particularly, the amount of protein adsorbed for 15, 23, and 94 hours of incubation was 30.68 µg per $cm^2$, 41.54 µg per $cm^2$, and 55.08 µg per $cm^2$, respectively. Protein adsorption was not detected for the non-coated control disks. These results are consistent with the FT-IR spectra showing the intensity of peaks at 1538 $cm^{-1}$, 2962 $cm^{-1}$, and 3307 $cm^{-1}$.

Sodium dodecyl sulphate-polyacrylamide gel electrophoresis (SDS-PAGE) was carried out to characterize the proteins incorporated into the coating. Protein samples were precipitated with 70% ethanol, centrifuged, collected, mixed with sample buffer, and denatured in boiling $H_2O$. Equivalent amounts of these samples (20 ul) were loaded into and separated by a 4–15% Tris-HCl gel. Bands were visualized using Coomassie Blue staining. The stained gels confirmed the results of the BCA assay that proteins were present in the hydroxyapatite coating. The staining patterns were similar for all time points, although the intensity of each band increased as a function of time. The bands indicated that proteins of 120 kD, 66 kD, 42 kD, 31 kD, 20 kD, and 18 kD were present in the coating. The proteins of 42 kD, 31 kD, 20 kD, and 18 kD were greater in amount as the bands at these positions on the gel were more intense than the bands of the proteins of 120 kD and 66 kD. The protein of 66 kD is likely albumin. These results indicate selective uptake of specific proteins from the Alpha Calf Fraction solution.

This example demonstrated a method of modifying a carbonated apatite-coated substrate by incubating the substrate a solution containing a protein and relatively low concentrations of calcium ions and phosphate ions to form a substrate with a coating comprising carbonated hydroxyapatite and incorporated proteins.

EXAMPLE 2

This example demonstrates another method of modifying a carbonated apatite-coated disk.

Titanium disks 25.2 mm in diameter and 3 mm thick were grit-blasted, ultrasonically cleaned, and coated with a nanoporous, nanocrystalline carbonated apatite coating. Apatite-coated and non-coated disks were each incubated in bovine calf serum containing 2.725 mM calcium ions and 3.226 mM phosphate ions (pH 7.3; 100 mL) at 37° C. for 68 hours. After incubation, samples were thoroughly washed by reverse-osmosis (RO)-purified $H_2O$ and dried at room temperature.

An X-ray diffraction pattern of the carbonated apatite coating before and after incubation with bovine calf serum revealed an increase in the intensity of diffraction peaks of apatite and a decrease in the strength of diffraction peaks of the titanium substrate, indicating the formation of new apatite on the apatite film. This was consistent with the results of the FT-IR spectra of the carbonated apatite coating before and after incubation with the bovine calf serum, which demonstrated an increase in intensity of both carbonate and phosphate bands after soaking in the bovine serum. These results show the growth of new apatite from serum on the apatite surface. The absence of a peak at 3563 $cm^{-1}$ indicated that the newly formed apatite layer is not hydroxyapatite. The presence of proteins in the newly formed apatite layer is indicated by the peak at around 1540 $cm^{-1}$. This is supported by EDS analysis, which demonstrated the presence of significantly higher levels of carbon in the coating obtained after incubating the disk with the bovine calf serum solution. The newly-formed apatite shows morphology that is different from the morphology of the apatite onto which it was formed, as demonstrated by scanning electron micrographs (SEMs) of the carbonated apatite coating before and after incubation with the bovine calf serum. Apatite was not detected on the surface of non-coated control specimens, indicating that the presence of a nanocrystalline carbonated apatite film on the disk before incubation with bovine calf serum is essential for the formation of the newly-formed apatite upon incubation. Through the BCA protein assay, an average of 37 μg protein per cm² of the coating was determined. In contrast, the amount of protein adsorbed to the non-coated control specimens were 0 μg. The pattern of the stained SDS-PAGE gels run on the coated specimens and the non-coated control specimens demonstrated that proteins of 92, 81, 75, 66, 41, and 27 kD were incorporated in the coating.

This example demonstrated a method of modifying a ceramic-coated titanium substrate by incubating the substrate with a solution comprising a protein and relatively higher concentrations of calcium ions and phosphate ions.

EXAMPLE 3

This example demonstrates the importance of nanocrystallinity and of nanoporosity of coatings in order for proteins to be incorporated into the coatings.

Pinnacle™ Sector Acetabular Cups (DePuy, Warsaw, Ind.) were plasma sprayed or biomimetically prepared to have a hydroxyapatite coating. Cups that were neither plasma sprayed nor biomimetically prepared served as control cups. Control, plasma sprayed, and biomimetically prepared cups were each incubated in bovine calf serum (100 mL) at 37° C. for 70 hours. After incubation, samples were thoroughly washed by RO-purified $H_2O$ and dried at room temperature. The cups were immersed in 50 mM EDTA solution overnight. The proteins present in the solutions were subjected to BCA total protein assay and analyzed by SDS-PAGE and reversed-phase high performance liquid chromatography (RP-HPLC).

The results of the BCA protein assay demonstrated that the amount of protein adsorbed to the plasma sprayed coating was about 350 μg, which was the same amount of protein adsorbed by the control cup that contained no coating. The protein adsorbed to the biomimetically prepared coating was about 1100 μg. The increase in protein adsorption is likely due, in part, to the microstructural differences between plasma sprayed and biomimetically prepared coatings. As was evident by SEM analysis, the plasma sprayed coating was dense, while the biomimetically prepared coating was nanoporous with a much larger surface area.

The SDS-PAGE pattern showed proteins incorporated in the coating formed on biomimetically coated cup. Remarkably, selective adsorption of proteins having molecular weights of about 30, 43, and 63 kD was observed besides the adsorption of albumin (66 kDa) which was the principal protein in serum. The HPLC results of proteins present in the coating on the biomimetically coated cup further confirmed the selective adsorption of proteins from bovine calf serum. The peaks eluted at 33.5 and 34% acetonitrile (ACN), which were originally two very small peaks in serum, became the majority of proteins incorporated in the coating on the biomimetically coated cup. The three strongest peaks including albumin in serum appeared to be in rather low quantity in the coating on the biomimetically coated cup.

This example demonstrates that the importance of nanoporosity of the ceramic coating for protein incorporation into the ceramic coating on the biocompatible substrate.

EXAMPLE 4

This example demonstrates a method of making a ceramic-coated implantable article.

A series of biocompatible substrates were incubated in different aqueous solutions comprising about 130 mM to about 200 mM sodium ions, about 3.5 to about 7 mM potassium ions, about 0.05 mM to about 5.0 mM magnesium ions, about 2 mM to about 10 mM calcium ions, about 96 mM to about 250 mM chloride ions, about 1 mM to about 6 mM phosphate ($HPO_4^{2-}$+$H_2PO_4^-$+$PO_4^{3-}$) ions, about 0.05 mM to about 50 mM $HCO^{3-}$ ions, about 0 mM to about 1 mM $SO_4^{2-}$ ions, and about 1 mM to about 100 mM tris(hydroxymethyl)aminomethane. The pH of the solutions at 37° C. was about 5 to about 9. The biocompatible substrates were placed in reactor vessels with the different solutions and incubated for about 0.1 to about 7 days at a temperature between about 20° C. to about 60° C. The incubations took place in an atmosphere comprising $CO_2$ and $O_2$ with about 0.001 to about 10 mole % $CO_2$. The flow rate at which the atmosphere was passed over the solutions was about 0 to about 10 liters per minute for every liter of solution. The biocompatible substrates subsequently were removed from the solutions and the reactor vessels.

SEM photomicrographs of the biocompatible substrates demonstrated that the coatings on the biocompatible substrates were uniform and covered all surfaces of the biocompatible substrates that were exposed to the solutions, including those that were recessed, undercut, flat, concave, convex, or of any other shape or orientation. The thickness of the coating on each biocompatible substrate was about 0.5–50 μm, and the adhesion strength of the coating to the substrate was in excess of 30 Mpa. FT-IR spectra on the coatings demonstrated that the coatings were a calcium phosphate apatite containing carbonate groups (peaks at 1350–1700 cm−1). Chemical analyses of the coatings dissolved in 0.002 N HCl confirmed that the coatings were similar to bone mineral. The molar ratio of $Ca^{2+}$ to $PO^{3-}$ was about 1.3–1.7. The molar ratio of $Ca^{2+}$ to $Mg^{2+}$ was up to 6.31. The molar ratio of $CO^{2-}$ to $PO_4^{3-}$ was about 0.025 to about 0.25. Energy dispersive X-ray analyses performed on the biocompatible substrates confirmed that the coatings on the substrates comprised calcium, phosphate and magnesium.

This example demonstrates a method of making an implantable article comprising (i) a biocompatible substrate and (ii) a bioactive surface coating chemically bonded to a substrate surface over at least a portion of the substrate, the coating comprising a non-hydroxyl containing carbonated calcium phosphate bone mineral nanocrystalline apatite with chemically adsorbed water, wherein the coating has a crystal size less than about 1 μm and has pores that are less than 1 μm in diameter.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of modifying a ceramic-coated implantable article, which method comprises:
   (a) providing an implantable article comprising a biocompatible substrate with a bioactive ceramic coating on at least a portion of the surface of the biocompatible substrate,
   (b) incubating at least a portion of the bioactive ceramic coating with a composition comprising (i) a biological agent, (ii) calcium ions in a concentration of about 0.01 mM to about 1 mM, (iii) phosphate ions in a concentration of about 0.01 mM to about 1 mM, and (iv) a liquid carrier, wherein the pH of the composition is between about 3.5 to about 9, and
   (c) removing the liquid carrier from the bioactive ceramic coating to yield a modified implantable article with a bioactive ceramic coating into which the biological agent is incorporated.

2. The method of claim 1, wherein the biological agent is an osteoinductive substance, an osteoconductive substance, or both.

3. The method of claim 2, wherein the biological agent is a protein.

4. The method of claim 3, wherein the protein is a non-collagenous protein selected from the group consisting of osteonectin, osteopontin, osteocalcin, and bone sialoprotein.

5. The method of claim 3, wherein the protein is a growth factor.

6. The method of claim 1, wherein the biological agent is an antibiotic.

7. The method of claim 1, wherein the bioactive ceramic coating of step (a) is a bioactive surface coating chemically bonded to the surface of the biocompatible substrate, wherein the coating comprises a non-hydroxyl containing carbonated calcium phosphate bone mineral nanocrystalline apatite with chemically adsorbed water, wherein the coating has a crystal size less than about 1 μm and has pores that are less than 1 μm in diameter.

8. The method of claim 1, wherein the concentration of the calcium ions is about 0.05 mM to about 0.5 mM, and wherein the concentration of the phosphate ions is about 0.05 mM to about 0.5 mM.

9. The method of claim 1, wherein the bioactive ceramic coating of the implantable article provided in step (a) is incubated with the composition for a period of about 30 minutes or more at a temperature between about 20° C. and the temperature at which the biological agent is inactivated or denatured.

10. The method of claim 1, wherein the liquid carrier is removed from the bioactive ceramic coating on the implantable article by drying the bioactive ceramic coating at a temperature below the temperature at which the biological agent is inactivated or denatured.

11. The method of claim 1, wherein the liquid carrier is removed from the bioactive ceramic coating on the implantable article by rinsing the bioactive ceramic coating with an aqueous solution and then drying the ceramic coating at a temperature below the temperature at which the biological agent is inactivated or denatured.

12. The method of claim 1, wherein the concentration of the biological agent in the bioactive ceramic coating of the modified implantable article is at least about 0.001 ng biological agent/mg coating.

13. The modified implantable article yielded by the method of claim 1.

14. A method of modifying a ceramic-coated implantable article, which method comprises:
   (a) providing an implantable article comprising a biocompatible substrate with a bioactive ceramic coating on at least a portion of the surface of the biocompatible substrate, wherein the bioactive ceramic coating comprises carbonated apatite of a first morphology,
   (b) incubating at least a portion of the bioactive ceramic coating with a composition comprising (i) a biological agent, (ii) calcium ions in a concentration of about 1 mM to about 10 mM, (iii) phosphate ions in a concentration of about 1 mM to about 10 mM, and (iv) a liquid carrier, wherein the pH of the composition is between about 3.5 to about 9, and
   (c) removing the liquid carrier from the bioactive ceramic coating to yield a modified implantable article with a bioactive ceramic coating into which the biological agent is incorporated, wherein the bioactive ceramic coating of the modified implantable article (i) has a second morphology that differs from the first morphology and (ii) does not comprise carbonated hydroxyapatite.

15. The method of claim 14, wherein the biological agent is an osteoinductive substance, an osteoconductive substance, or both.

16. The method of claim 15, wherein the biological agent is a protein.

17. The method of claim 16, wherein the protein is a non-collagenous protein selected from the group consisting of osteonectin, osteopontin, osteocalcin, and bone sialoprotein.

18. The method of claim 16, wherein the protein is a growth factor.

19. The method of claim 14, wherein the biological agent is an antibiotic.

20. The method of claim 14, wherein the bioactive ceramic coating of step (a) is a bioactive surface coating chemically bonded to the surface of the biocompatible substrate, wherein the coating comprises a non-hydroxyl containing carbonated calcium phosphate bone mineral nanocrystalline apatite with chemically adsorbed water, wherein the coating has a crystal size less than about 1 μm and has pores that are less than 1 μm in diameter.

21. The method of claim 14, wherein the concentration of the calcium ions is about 2 mM to about 3 mM, and wherein the concentration of the phosphate ions is about 3 mM to about 4 mM.

22. The method of claim 14, wherein the bioactive ceramic coating of the implantable article provided in step (a) is incubated with the composition for a period of about 30 minutes or more at a temperature between about 20° C. and the temperature at which the biological agent is inactivated or denatured.

23. The method of claim 14, wherein the liquid carrier is removed from the bioactive ceramic coating of the implantable article by drying the bioactive ceramic coating at a temperature below the temperature at which the biological agent is inactivated or denatured.

24. The method of claim 14, wherein the liquid carrier is removed from the ceramic coating on the implantable article by rinsing the bioactive ceramic coating with an aqueous solution and then drying the bioactive ceramic coating at a temperature below the temperature at which the biological agent is inactivated or denatured.

25. The method of claim 14, wherein the concentration of the biological agent in the bioactive ceramic coating on the modified implantable article is at least about 0.001 ng biological agent/mg coating.

26. The modified implantable article yielded by the method of claim 14.

27. An implantable article comprising:
(i) a biocompatible substrate, and
(ii) a bioactive surface coating chemically bonded to a substrate surface over at least a portion of the substrate, wherein the coating comprises a non-hydroxyl containing carbonated calcium phosphate bone mineral nanocrystalline apatite with chemically adsorbed water, wherein the coating has a crystal size less than about 1 µm and has pores that are less than 1 µm in diameter, and wherein a biological agent is incorporated into the pores.

28. The implantable article of claim 27, wherein the coating has a thickness of about 0.005 µm to about 50 µm.

29. The implantable article of claim 27, wherein the coating has a molar ratio of carbonate groups to phosphate groups of about 1:100 to about 1:3.

30. The implantable article of claim 29, wherein the coating contains one or more substances selected from the group consisting of sodium, calcium, magnesium, sulfate, silicate, chlorine, and mixtures thereof.

31. The implantable article of claim 30, wherein the coating contains magnesium and calcium, and the atomic ratio of magnesium to calcium in the coating is about 1:5000 to about 1:4.

32. The implantable article of claim 27, wherein the substrate is selected from a group consisting of silicon, metals, ceramics, and polymers.

33. The implantable article of claim 32, wherein the substrate is a metal selected from the group consisting of titanium, titanium alloys, cobalt-chromium alloys, tantalum, tantalum alloys, and stainless steel.

34. The implantable article of claim 32, wherein the substrate is a polymer selected from the group consisting of ultrahigh molecular weight polyethylene, polyethylene oxide, polylactic acid, polyglycol acid, and copolymers of polylactic acid and polyglycol acid.

35. The implantable article of claim 27, wherein the substrate is a component of a joint prosthesis.

36. A method of preparing the implantable article of claim 27, which method comprises:
(a) providing a biocompatible substrate,
(b) incubating at least a portion of a surface of the biocompatible substrate with a composition comprising (i) a biological agent, (ii) calcium ions in a concentration of about 1 mM to about 10 mM, (iii) phosphate ions in a concentration of about 1 mM to about 10 mM, and (iv) a liquid carrier, wherein the pH of the composition is between about 3.5 to about 9, and
(c) removing the liquid carrier from the biocompatible substrate to yield an implantable article with a bioactive surface coating chemically bonded to a substrate surface over at least a portion of the substrate, wherein the coating comprises a non-hydroxyl containing carbonated calcium phosphate bone mineral nanocrystalline apatite with chemically adsorbed water, wherein the coating has a crystal size less than about 1 µm and has pores that are less than 1 µm in diameter, and wherein a biological agent is incorporated into the pores.

* * * * *